United States Patent [19]
Williams

[11] Patent Number: 5,463,126
[45] Date of Patent: Oct. 31, 1995

[54] PROCESS FOR PREPARING SERTRALINE

[75] Inventor: Michael T. Williams, Sandwich, United Kingdom

[73] Assignee: Pfizer Inc., New York, N.Y.

[21] Appl. No.: 178,272

[22] PCT Filed: Jul. 3, 1992

[86] PCT No.: PCT/EP92/01497

§ 371 Date: Jan. 10, 1994

§ 102(e) Date: Jan. 10, 1994

[87] PCT Pub. No.: WO93/01162

PCT Pub. Date: Jan. 21, 1993

[30] Foreign Application Priority Data

Jul. 11, 1991 [GB] United Kingdom .................. 9114947

[51] Int. Cl.$^6$ .................. C07C 233/03; C07C 233/04; C07C 231/18

[52] U.S. Cl. .................. 564/222; 564/217; 564/218; 564/221

[58] Field of Search .................. 564/200, 192, 564/215, 218, 219, 221, 222; 574/625, 629, 630

[56] References Cited

U.S. PATENT DOCUMENTS

| | | | |
|---|---|---|---|
| 4,536,518 | 8/1985 | Welch et al. | 514/647 |
| 4,882,339 | 11/1989 | Wasley | 514/319 |
| 5,071,875 | 12/1991 | Horn et al. | 514/613 |

FOREIGN PATENT DOCUMENTS 0030081  6/1981  European Pat. Off. .

*Primary Examiner*—Shailendra Kumar
*Attorney, Agent, or Firm*—Peter C. Richardson; Paul H. Ginsburg

[57] ABSTRACT

The invention provides the substantially geometrically pure cis-stereoisomeric form of a compound of formula (I) and the substantially geometrically and optically pure cis-stereoisomeric form of a compound of formula (II):

wherein $R^1$ is H or $C_1$–$C_4$ alkyl, together with processes for their preparation. The compounds are intermediates for the preparation of the antidepressant agent known as sertraline.

16 Claims, No Drawings

PROCESS FOR PREPARING SERTRALINE

This application is a 371 of PCT/US 92/01497 filed Jul. 3, 1992.

BACKGROUND OF THE INVENTION

This invention relates to novel cis-N-alkanoyl-N-methyl-4-(3,4-dichlorophenyl)-1,2,3,4-tetrahydro-1-naphthylamine analogues, which are key intermediates in a new process for preparing sertraline, together with intermediates thereto and processes for the preparation thereof.

A specific embodiment of the invention relates to the (1S,4S)-stereoisomeric form of such cis-N-alkanoyl-N-methyl-4 -(3,4-dichlorophenyl)-1,2,3,4-tetrahydro-1-naphthylamines, intermediates thereto and processes for the preparation thereof. These novel cis-1,4-disubstituted tetrahydronaphthylamines and processes thereto are particularly advantageous in the synthesis of the antidepressant agent known as sertraline, or cis-(1S,4S)-N-methyl- 4-(3,4-dichlorophenyl)-1,2,3,4-tetrahydro-1-naphthylamine, which is disclosed in U.S. Pat. No. 4,536,518 and in the Journal of Medicinal Chemistry, 1984, 27, 1508.

SUMMARY OF THE INVENTION

The novel compounds of the present invention have been made available by the unexpected discovery that the required cis-isomer may be generated stereoselectively, in high yield, by catalytic hydrogenation of the appropriate N-alkanoyl-N-methyl- 4-(3,4-dichlorophenyl)-1,2-dihydro-1-naphthylamine precursor, allowing ready removal of the unwanted trans-ismore. More importantly, when the precursor itself is optically pure and the 1-(N-alkanoyl)methylamino substituent possesses the S-configuration, catalytic hydrogenation thereof affords the cis- (1S,4S)-enantiomer in high yield and with high stereoselectivity, thus obviating the need for a final stage optical resolution to separate sertraline from the unwanted cis-(1R,4R)-enantiomer.

Thus the present invention provides:

a) the substantially geometrically pure cis-stereoisomeric form, consisting of a racemic mixture of the cis-(1S,4S) and the cis-(1R,4R) enantiomers, of a compound of formula:

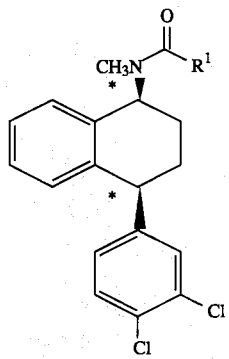

(I)

wherein $R^1$ is H or $C_1$–$C_4$ alkyl and * denotes an unresolved asymmetric centre;

b) the substantially geometrically and optically pure cis-stereoisomeric form, consisting of the cis-(1S,4S) enantiomer, of a compound of formula:

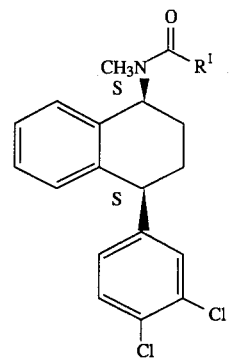

(II)

wherein $R^1$ is H or $C_1$–$C_4$ alkyl and S represents the absolute configuration of a resolved asymmetric centre;

c) processes for preparing the substantially geometrically pure cis-stereisomeric form of a compound of formula (I) or the substantially geometrically and optically pure cis-stereoisomeric form of a compound of formula (II) by subjecting, respectively, a compound of formula:

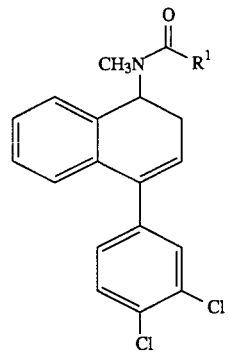

(III)

or

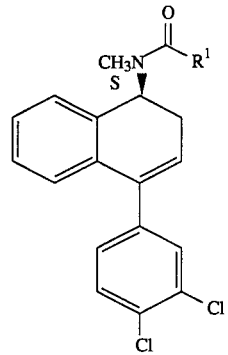

(IV)

wherein $R^1$ and S are as previously defined for formulae (I) and (II), in a suitable solvent, to hydrogenation in the presence of platinum or palladium as catalyst;

d) novel intermediates of formulae (III) and (IV).

Alkyl groups containing three or four carbon atoms may be straight or branched chain.

The term "substantially geometrically pure" means that the compounds of the formula (I) contain less than 4%, and preferably less than 2%, of the undesired diastereoisomeric pair of trans-( 1S,4R) and (1R,4S)-enantiomers. The term "substantially geometrically and optically pure" means that the compound of formula (II) contains less than 4%, and preferably less than 2%, of the undesired trans-(1S,4R)-enantiomer.

In the above definitions of the compounds of formulae (I), (II), (III) and (IV), preferably R¹ is H or methyl.

The compounds provided by the present invention may be prepared as follows:

DETAILED DESCRIPTION OF THE INVENTION

1. A compound of formula (I) is prepared by hydrogenation of a compound of formula (III), in the presence of platinum oxide, in a suitable solvent, e.g. tetrahydrofuran, ethyl acetate or ethanol. Typically, the reaction is conducted under pressure at about 50 p.s.i. (3.45 bar) of hydrogen and at a temperature of from 20° to 25° C. for 1 to 2 hours. The product of formula (I) may then be isolated and purified by conventional techniques, e.g. by removal of the catalyst by filtration, evaporation under vacuum of the filtrate, and then crystallisation of the crude residue to remove minor amounts of the unwanted trans- isomer. Alternatively, the separation of cis- and trans-isomers can be effected after removal of the N-alkanoyl group to furnish a compound of formula (IX), wherein * is as previously defined, in the next stage of the synthetic sequence depicted in Scheme 1.

Scheme 1

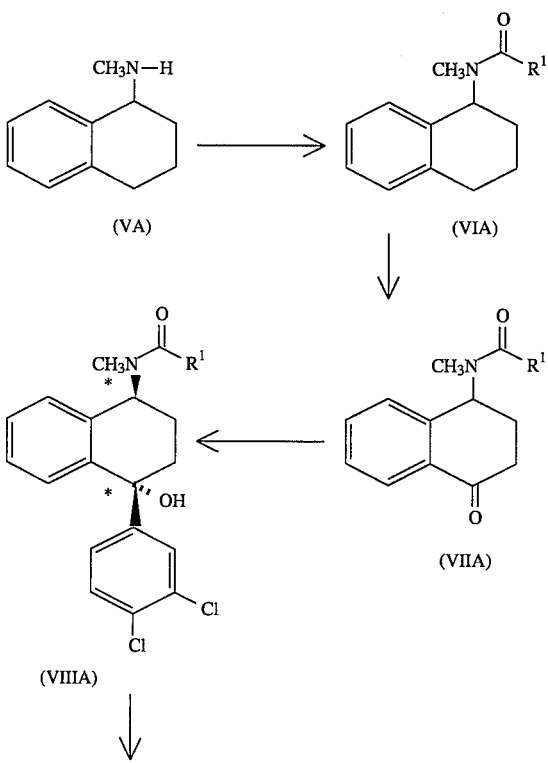

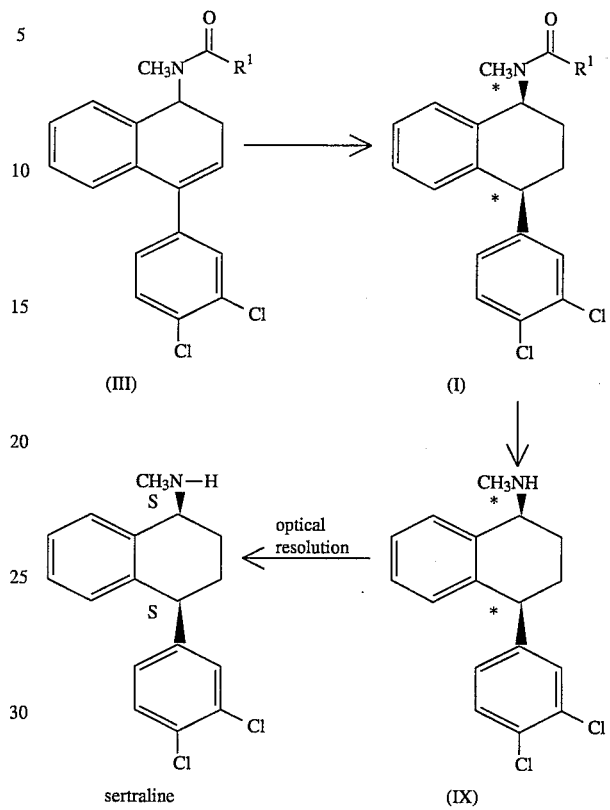

-continued
Scheme 1

The N-alkanoyl group of a compound of formula (I), the major isomer of the aforementioned crude residue, is removed by hydrolysis using an aqueous inorganic base such as an alkali metal hydroxide salt, preferably potassium hydroxide, as a 10 molar solution in water. Typically the hydrolysis is carried out in ethylene glycol at the reflux temperature of the reaction medium for from 2 hours to 4 days. For a compound of formula (I) wherein R¹ is H, the N-alkanoyl group is preferably removed by acidic hydrolysis using a mineral acid, e.g. hydrochloric acid, in a suitable solvent such as 2-propanol, 1,4-dioxan or ethyl acetate, at the reflux temperature of the reaction medium for from 2 to 8 hours. The product (IX) is then isolated and purified by conventional procedures, e.g. extractive work-up, optional column chromatography to remove minor amounts of the unwanted trans-isomer, and conversion to the hydrochloride salt. This salt may then be processed via the resolution procedure described in U.S. Pat. No. 4,536,518 to provide the cis-(1S,4S)-enantiomer (sertraline).

A compound of formula (III) required for the preparation of a compound of formula (I) may be obtained by the route depicted in Scheme 1, wherein R¹, * and S are as previously defined, using conventional procedures.

Thus, typically, a compound of formula (VIA) wherein R¹ is $C_1$-$C_4$ alkyl can be prepared by acylating a compound of formula (VA) with either an acyl halide of formula ($C_1$-$C_4$ alkyl)CO(Cl or Br) or with an acid anhydride of formula [($C_1$-$C_4$ alkyl)CO]$_2$O. When an acyl halide is employed the reaction may be carried out at from 0° to 25° C., preferably at from 5° to 10° C., in a suitable organic solvent, e.g. dichloromethane, and in the presence of an acid acceptor, e.g. triethylamine. When an acid anhydride is used the reaction may be conducted at up to the reflux temperature of the reaction medium, preferably at 100° C., in a suitably compatible solvent, e.g. a carboxylic acid of formula ($C_1$–$C_4$ alkyl)$CO_2H$. To obtain a compound of formula (VIA) wherein $R^1$ is H, compound (VA) is formylated using acetic-formic anhydride which may be generated by the addition of 98% formic acid to stirred acetic anhydride, typically between 0° and 10° C. The freshly prepared mixed anhydride is then reacted with compound (VA) in an appropriate solvent, e.g. 98% formic acid, at from 5° to 25° C.

Conversion of a compound of formula (VIA) to a ketone of formula (VIIA), via a benzylic oxidation reaction, can be effected with a variety of oxidising agents such as an inorganic permanganate salt, ammonium cerium(IV) nitrate, cobalt(III) acetate or 2,3-dichloro-5,6-dicyano-1,4-benzoquinone, in a suitable solvent. Preferably, the reaction is carried out using 3–5 molecular equivalents of potassium permanganate in aqueous acetone in the presence of a buffering reagent such as an alkali, or alkaline earth, metal salt, e.g. magnesium sulphate. The oxidant may be added in portions in a controlled manner, in order to moderate the potentially vigorous reaction, to a solution of the substrate (VIA) at from 5° to 30° C. Subsequent to this addition, warming of the reaction mixture at from 30° to 50° C. may be required in order to complete the oxidation.

A compound of formula (VIIIA) can be prepared stereoselectively from a compound of formula (VIIA) using a 3,4-dichlorophenylmagnesium halide, preferably the iodide, under standard Grignard reaction conditions. Thus, typically, a solution of the ketonic substrate (VIIA) in a suitably compatible solvent, e.g. dry toluene or dry tetrahydrofuran, is added to a freshly prepared solution of the Grignard reagent in an appropriate solvent such as dry diethyl ether, at a temperate of from 5° to 25° C., under anhydrous conditions. The reaction is allowed to proceed at from 20°–25° C. for from 4 to 24 hours and the mixture may be heated under reflux for up to 1 hour, if necessary, to promote a better conversion of (VIIA) to (VIIIA). Minor amounts of the trans-alcohol may be removed, if required, by column chromatography and/or crystallisation.

Transformation of a tertiary alcohol of formula (VIIIA) to an alkene of formula (III) can be carried out under a variety of conditions such as heating alone, with phosphorus oxychloride in pyridine, with sodium acetate in acetic anhydride, or with 4-dimethylaminopyridine in acetic anhydride. Preferably, however, the dehydration is effected by using a Lewis acid in a suitable solvent, e.g. boron trifluoride in glacial acetic acid, at about ambient temperature.

2. A compound of formula (II) may be prepared from a compound of formula (IV) in a manner analogous to that described above for the preparation of compound (I) from compound (III). In this case, however, the major product from the catalytic hydrogenation is the single cis-(1S,4S)-enantiomer (II). Again, the separation of the cis- and trans-isomers is most conveniently accomplished after removal of the N-alkanoyl group, which furnishes sertraline directly (see Scheme 2), although crystallisation of the crude hydrogenation product suffices to remove minor amounts of the unwanted trans-(1S,4R)-enantiomer.

The N-alkanoyl group of compound (II), the major component of the aforementioned hydrogenation reaction, may be removed by the hydrolysis methods described hereinbefore for the conversion of (I) to (IX)—see Scheme 1.

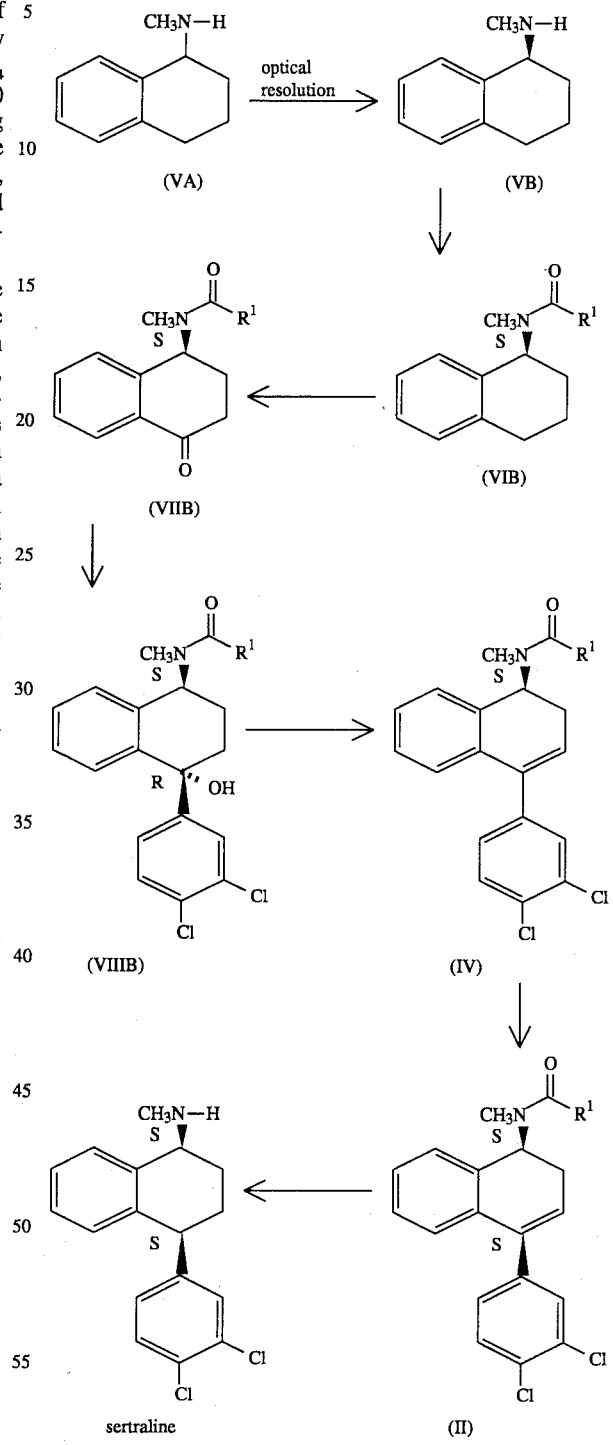

A compound of formula (IV) required for the preparation of a compound of formula (II) may be obtained from compound (VB) by the route depicted in Scheme 2, wherein $R^1$, * and S are as previously defined, using the procedures described for the preparation of a compound of formula (III) from compound (VA)—see Scheme 1. In this case, however, prior resolution of the amine (VA) is effected to provide the optically pure S-enantiomer (VB). The resolution is carried out in a conventional manner by fractional crystallisation of a salt of the amine (VA), formed with an optically pure acid such as a sulphonic or carboxylic acid, and preferably, (2S,3S) (−) tartaric acid or N-acetyl-(S)-phenylalanine, from an appropriate solvent e.g. water or ethanol. The free amine (VB) is then liberated by treatment of the resolved amine salt with a base, typically an aqueous solution of sodium or potassium hydroxide.

The amine (VB) may also be obtained by asymmetric reduction of the imine precursor, which is directly accessible from α-tetralone and methylamine, by methods well known to persons skilled in the art.

The invention will now be more particularly illustrated by the following experimental Examples. The purity of the compounds was monitored by thin layer chromatography (TLC) using Merck Kieselgel 60 $F_{254}$ plates. Routine $^1$H-nuclear magnetic resonance (nmr) spectra were recorded using a Nicolet QE-300 spectrometer and $^{13}$C nmr spectra were recorded using a Bruker 250 spectrometer; they were in all cases consistent with the proposed structures. Nuclear Overhauser effect (nOe) experiments were conducted using a Bruker 250 spectrometer.

EXAMPLE 1

N-(1,2,3,4-Tetrahydro-1-naphthyl)-N-methylacetamide

A stirred solution of N-methyl-1,2,3,4-tetrahydro-1-naphthylamine hydrochloride (70.2 g) in water (400 ml) was basified to pH about 11, by addition of 10N aqueous sodium hydroxide solution (40 ml), and extracted with dichloromethane (250 ml, then 100 ml). The combined, stirred organic extracts were treated with triethylamine (40.5 g), cooled to 5° C., and acetyl chloride (31.4 g) was then added dropwise over 40 minutes, keeping the reaction temperature below 10° C. After being stirred for a further 20 minutes the solution was washed with water (100 ml), 1N aqueous sodium hydroxide solution (100 ml) and water (100 ml). Evaporation under vacuum of the dichloromethane solution gave the title compound as a pale brown mobile oil (72.8 g, 100%); Rf 0.69 (silica; chloroform, methanol; 95:5). GLC assay on a 2.1 m×4 mm 3% OV-17 column, temperature programmed from 100° C. to 250° C. at 10° C./minute, showed the product to be 99.9% pure (retention time 13.8 minutes).

$^1$H-nmr (300 MHz, $CDCl_3$)

δ=1.64–1.92 (m, 2H), 1.95–2.14 (m, 2H), 2.13 and 2.19 (2 acetyl $CH_3$ rotamer singlets, 3H), 2.67 and 2.72 (2 NMe rotamer singlets, 3H), 2.76–2.90 (m, 2H), 4.97–5.07 and 5.91–6.00 (2 rotamer multiplets, 1H), 6.98–7.24 (m, 4H) p.p.m.

EXAMPLE 2

N-(1,2,3,4-Tetrahydro-4-keto-1-naphthyl)-N-methylacetamide

A stirred solution of N-(1,2,3,4-Tetrahydro-1-naphthyl)-N-methylacetamide (93.4 g) in acetone (1050 ml) was treated with magnesium sulphate heptahydrate (139.4 g) and water (350 ml) and the mixture was chilled to 5° C. Solid potassium permanganate (232.3 g) was added portionwise over 2 hours with cooling to keep the reaction temperature below 35° C. The mixture was warmed, held at 45° to 50° C. for 40 minutes, filtered and the solids washed with acetone (5×100 ml). The combined filtrate and washes were evaporated under vacuum to remove acetone, and the resulting aqueous solution was extracted with dichloromethane (3×150 ml). The organic extracts were evaporated under vacuum to give an oil (76 g) which was stirred with diethyl ether (200 ml); a solid separated and was collected by filtration (69 g). This solid was reslurried with fresh diethyl ether (100 ml), collected and dried to give the title compound as white crystals (61.7 g, 61.8%), m.p. 101°–103° C.; Rf 0.54 (silica; chloroform, methanol; 95:5). Found: C,71.97; H,6.96; N,6.51.$C_{13}H_{15}NO_2$ requires C,71.85; H,6.96; N 6.44%. GLC assay on a 2.1 m×4 mm 3% OV-17 column, temperate programmed from 100° to 220° C. at 10° C./minute, showed the product to be 99.2% pure (retention time 22.0 minutes).

$^1$H-nmr (300 MHz, $CDCl_3$)

δ=2.17–2.33 (m, 2H), 2.29 and 2.31 (2 acetyl $CH_3$ rotamer singlets, 3H), 2.70–2.94 (m, 2H), 2.77 and 2.83 (2 NMe rotamer singlets, 3H), 5.18–5.26 and 6.19–6.28 (2 rotamer multiplets, 1H), 7.10–7.24 (2 aromatic rotamer doublets, 1H), 7.36–7.51 (m, 1H) 7.53–7.66 (m, 1H), 8.07–8.14 (d, 1H) p.p.m.

EXAMPLE 3

(1R*, 4S*)-N-[4-(3,4-Dichlorophenyl)-1,2,3,4-tetrahydro-4-hydroxy-1-naphthyl]-N-methylacetamide Magnesium turnings (2.04 g) and a crystal of iodine were stirred in dry diethyl ether (24 ml) as a solution of 1,2-dichloro-4-iodobenzene (23.17 g) in dry diethyl ether (60 ml) was added over 15 minutes. The mixture was stirred for 15 minutes and refluxed for a further 15 minutes to complete formation of the Grignard reagent. The mixture was cooled to room temperature and a solution of N-(1,2,3,4-tetrahydro-4-keto-1-naphthyl)-N-methylacetamide (12.3 g) in dry tetrahydrofuran (134 ml) was added over 5 mutes. The mixture was stirred for 4 hours at room temperature, heated under reflux for 30 minutes, cooled and treated with 4N aqueous sulphuric acid (30 ml). The lower aqueous phase was separated and discarded, dichloromethane was added, and the solution was washed with water (2×25 ml). The organic layer was evaporated under vacuum to give a mixture of racemic cis-(1R*, 4S*)- and trans-(1R*, 4R*)-isomers (ratio 87:13 respectively by nmr spectroscopy techniques) as a light brown gum (24.5 g) which was stirred with diethyl ether (150 ml) for 1 hour, then filtered, to give the title compound as cream crystals (10.2 g, 49.5%), m.p. 146°–148° C.; Rf 0.41 (silica; chloroform, methanol; 95:5). Found: C,62.96; H,5.24; N,4.00 $C_{19}H_{19}Cl_2NO_2$ requires C,62.65; H,5.26; N 3.85%. GLC assay on a 2.1 m×4 mm 3% OV-17 column, temperature programmed from 100° to 275° C. at 10° C./minute, showed the product to be 96% pure (retention time 41.5 minutes) containing 3% recovered ketone.

$^1$H-nmr (300 MHz, $CDCl_3$)

δ=1.48–1.65 (m, 1H), 1.73–1.95 (m, 1H), 2.18–2.41 (m, 2H), 2.21 and 2.29 (2 acetyl $CH_3$ rotamer singlets, 3H), 2.66 and 2.73 (2 NMe rotamer singlets, 3H), 5.06–5.15 and 5.95–6.03 (2 rotamer multiplets, 1H), 6.90–7.47 (m, 7H) p.p.m.

EXAMPLE 4

N-[4-(3,4-Dichlorophenyl)-1,2-dihydro-1-naphthyl]-N-methylacetamide

A solution of (1R*, 4S*)-N-[4-(3,4-dichlorophenyl)-1,2,3,4-tetrahydro-4-hydroxy-1-naphthyl]-N-methylacetamide (5 g) in glacial acetic acid (50 ml) was treated with boron trifluoride etherate (2 ml) and stirred for 2.5 hours at ambient temperature. The solution was poured into water (100 ml), extracted with dichloromethane (2×50 ml) and the combined extracts washed with saturated aqueous sodium bicarbonate solution (200 ml). The dichloromethane solution was then evaporated under vacuum and the residual foam (4.8 g) was chromatographed on silica (200 g) eluting with hexane-chloroform (1:2), chloroform and then chloroform-methanol (9:1). Evaporation under vacuum of the requisite fractions gave the product as an oil (3.6 g, 75.7%); Rf 0.22 (silica; chloroform) and 0.58 (silica; chloroform, methanol; 95:5). GLC assay on a 2.1 m×4 mm 3% OV-17 column, run isothermally at 250° C., showed the product to be 98% pure.
$^1$H-nmr (300MHz CDCl$_3$)

δ=2.24 and 2.25 ( 2 acetyl CH$_3$ rotamer singlets, 3H), 2.50–2.75 (m, 2H), 2.91 and 2.93 (2 NMe rotamer singlets, 3H), 5.19–5.30 and 6.02–6.08 (2 rotamer multiplets, 1H), 6.09–6.19 (m, 1H), 6.97–7.52 (m, 7H) p.p.m.

EXAMPLE 5 cis-(1R*,4R*)-N-[4-(3,4-Dichlorophenyl)-1,2,3,4-tetrahydro-1-naphthyl]-N-methylacetamide A solution of N-[4-(3,4-dichlorophenyl)-1,2-dihydro-1-naphthyl]-N-methylacetamide (0.5 g) in tetrahydrofuran (12.5 ml) was hydrogenated over platinum oxide (0.1 g) at room temperature and 50 p.s.i. (3.45 bar) for 1.25 hours. The catalyst was removed by filtration, and the filtrate was evaporated under vacuum to give the crude product as an oil (0.50 g, 99.4%); Rf 0.19 (silica; chloroform). A $^1$H-nmr assay (300 MHz, CDCl$_3$) of this material showed it to be a 70:30 mixture of the cis-isomer (δ=4.17–4.28 ppm, m, for the H$_4$ proton) and the trans-isomer (δ=4.00–4.12 ppm, m, for the H$_4$ proton), respectively.

The separation of cis- and trans-isomers is more effectively carried out after removal of the acetyl group. However, crystallisation of a sample of the crude product from diethyl ether provided a reference sample of the title compound as white crystals, m.p. 93°–95° C., Rf 0.60 (silica; chloroform, methanol; 95:5). Found: C,65.99; H,5.45; N,4.54. C$_{19}$H$_{19}$Cl$_2$NO requires C,65.52; H,5.50: N,4.02%.

EXAMPLE 6 cis-(1R*,4R*)-N-Methyl-4-(3,4-dichlorophenyl)-1,2,3,4-tetrahydro-1-naphthylamine hydrochloride A solution of cis-(1R*,4R*)-N-[4-(3,4-dichlorophenyl)-1,2,3,4-tetrahydro-1-naphthyl]-N-methylacetamide (2.0 g cis/trans mixture) in ethylene glycol (40 ml) was treated with 10N aqueous potassium hydroxide solution (20 ml) and then heated under reflux for 81 hours. The cooled mixture was diluted with water (25 ml), acidified to pH 1 with concentrated hydrochloric acid (21 ml) and extracted with dichloromethane (2×50 ml). The extracts were evaporated under vacuum to give a yellow gum (1.83 g) which was chromatographed on silica (73 g), eluting with chloroform and then a chloroform/methanol mixture. Chloroform eluted recovered starting material (1.46 g, 73% recovery), while the chloroform/methanol mixture eluted first the product as its free base (0.080 g, 4.5%) and then mixed cis- and trans-fractions.

The cis-amine base (0.080 g) in 2-propanol (0.6 ml) was treated with a 2-propanolic solution of hydrogen chloride (0.3 ml of 24% w/v solution) and granulated for 2 hours. Filtration gave the product (0.078 g; 3.8% step yield) as white crystals, m.p. 275°–277° C.; Rf 0.13 (silica; chloroform, methanol; 95:5). Found: C,59.89; H,5.42; N,4.16. C$_{17}$H$_{17}$Cl$_2$N;HCl requires C,59.58; H,5.29; N,4.09%.

EXAMPLE 7

(S)(+)-N-Methyl-1,2,3,4-tetrahydro-1-naphthylamine (a) A cold solution of N-methyl-1,2,3,4-tetrahydro-1-naphthylamine (3.87 g) in ethanol (77.5 ml) was added to a hot solution of N-acetyl-(S)-phenylalanine (5.0 g) in ethanol (75 ml). The clear solution was chilled to induce crystallisation and refrigerated at 4° C. overnight. Filtration, washing with ethanol (2×5 ml) and drying gave the crude N-acetyl-(S)-phenylalanine salt of the (S)-amine (3.61 g, 40.7%) as white crystals, m.p. 190°–193° C. Recrystallisation of 2.7 g of this material from ethanol (60 ml) gave the N-acetyl-(S)-phenylalanine salt of the title compound (2.04 g, 61.7% overall yield based on available enantiomer) as white crystals, m.p. 191°–193° C., [α]$_D$+ 34.1° (c=0.49, water). Found: C,71.74; H,7.56; N,7.61. C$_{22}$H$_{28}$N$_2$O$_3$ requires C,71.71; H,7.66; N,7.60%.

A sample of this salt (0.7 g) was stirred in a mixture of water (5 ml) and dichloromethane (5 ml), then 5N aqueous sodium hydroxide solution was added dropwise to adjust the pH of the aqueous phase to 11. The phases were separated and the aqueous phase was washed with dichloromethane. Evaporation under vacuum of the combined organic layers gave the title compound as a colourless oil (0.30 g, 97.9% from salt), [α]$_D$+ 10.1° (c=5, EtOH); Rf 0.37 (silica; ethyl acetate, methanol, 15.1N aqueous NH$_3$; 80:20:1).

(b) A solution of (2S,3S) (–) tartaric acid (160.3 g in water (50 ml) was treated with N-methyl-1,2,3,4-tetrahydro-1-naphthylamine (172.2 g), the temperature being allowed to rise to 35° C. The resulting clear solution was chilled to induce crystallisation and granulated for several hours at 5° C. Filtration, washing with water (3×50 ml) and drying gave the crude (–) tartaric acid salt of the (S)-amine (198.2 g) as a white solid, m.p. 99°–106° C. Fractional recrystallisation from water gave the (–)tartaric acid salt of the title compound (59.3 g, 33.7% overall based on available enantiomer) as white crystals, m.p. 107°–109° C., [α]$_D$–12.4° (c=4.96, water). Found: C,54.82; H,7.09; N,4.21. C$_{15}$H$_{21}$NO$_6$;H$_2$O requires C,54.70; H,7.04; N,4.25%.

The salt (53.6 g) was dissolved in water (150 ml) by warming to 40° C. The solution was basified to pH 11 by dropwise addition of 5N aqueous sodium hydroxide solution, and the mixture was extracted with dichloromethane (2×150 ml). Evaporation under vacuum of the combined organic extracts gave the title compound as a colourless oil (26.0 g, 96.4% from salt), [α]$_D$+10.4° (c=5, EtOH). A sample of this oil (0.16 g) was acylated with (+)-α-methoxy-α-(trifluoromethyl)phenylacetyl chloride (0.5 g) in carbon tetrachloride (2.5 ml) containing pyridine (0.75 ml). Isolation of the amide and $^1$H-nmr assay using the method of Mosher (J. Org. Chem., 1969, 34, 2543) showed the title compound to be a 95:5 mixture of the (S)- and (R)-enantiomers, respectively.

EXAMPLE 8

(S)(–)-N-(1,2,3,4-Tetrahydro-1-naphthyl)-N-methylformamide

Acetic anhydride (73.5 g) was chilled and stirred as 98% formic acid (44.2 g) was added over 30 minutes keeping the temperature below 10° C. The resulting solution of acetic-formic anhydride was stirred for a further 15 minutes at 5° C. and added over 5 minutes to a stirred, chilled solution of (S)(+)-N-methyl-1,2,3,4-tetrahydro-1-naphthylamine (26 g)

in 98% formic acid (26 ml). The reaction solution was stirred at ambient temperature for 1 hour, poured into an ice-water mixture (200 g) and basified with 10N aqueous sodium hydroxide solution (about 250 ml) to pH 10; the mixture was then extracted with dichloromethane (3×200 ml). The combined extracts were back-washed with 1N aqueous hydrochloric acid (100 ml ), then water (100 ml), and evaporated under vacuum to give the title compound (28.69 g, 94%) as a solid, m.p. 52°–54° C.; Rf 0.80 (silica; chloroform, methanol; 95:5). A chiral HPLC assay on an acetylated β-cyclodextrin column showed this material to be a 94:6 mixture of the (S)- and (R)-enantiomers, respectively.

A sample of the product (1.5 g) was crystallised from a mixture of ethyl acetate (2 ml) and hexane (15 ml) to give a purified sample of the title compound (0.79 g, 52.7% recovery) as white crystals, m.p. 55°–56° C., $[\alpha]_D$–19.9° (c=5, EtOH), containing no detectable (R)-enantiomer on chiral HPLC assay. Found: C,76.29; H,7.87; N,7.47. $C_{12}H_{15}NO$ requires C,76.16; H,7.98; N,7.40%.

EXAMPLE 9

(S)(–)-N-(1,2,3,4-Tetrahydro-4-keto-1-naphthyl)-N-methylformamide

To a chilled solution of (S)(–)-N-(1,2,3,4-tetrahydro-1-naphthyl)-N-methylformamide (26 g) in acetone (585 ml) was added magnesium sulphate heptahydrate (78 g), water (195 ml) and the, portionwise over 1 hour, potassium permanganate (104 g). The mixture was stirred for 6 hours with water-bath cooling to keep the reaction temperature below 30° C., then filtered and the cake washed with acetone (2×150 ml). The filtrate and washes were combined, treated with 10% aqueous sodium metabisulphite solution (240 ml) and extracted with dichloromethane (600 ml and then 300 ml). The combined extracts were evaporated under vacuum to an oil (21.1 g) which was chromatographed on silica (805 g), eluting with a dichloromethane/methanol mixture (98:2) to give the product as an oil (12.36 g, 44.3%); Rf 0.18 (silica; ethyl acetate) and 0.58 (silica; chloroform, methanol; 95:5).

A sample of the product (1.16 g) was triturated with diethyl ether (20 ml) to induce crystallisation, giving a purified sample of the title compound (0.75 g), m.p. 90°–92° C., $[\alpha]_D$–52.7° (c=0.5, EtOH). Found: C,70.42; H,6.46; N,6.89. $C_{12}H_{13}NO_2$ requires C,70.92; H,6.45; N,6.64%.

EXAMPLE 10

(1S,4R)(+)-N-[4-(3,4-Dichlorophenyl)-1,2,3,4-tetrahydro-4-hydroxy-1-naphthyl]-N-methylformamide Magnesium turnings (0.89 g) and a crystal of iodine were stirred in dry diethyl ether (25 ml) as a solution of 1,2-dichloro-4-iodobenzene (10.08 g) in diethyl ether (25 ml) was added over 10 minutes. After the exotherm subsided, the mixture was heated under reflux for a further 15 minutes to complete consumption of the magnesium metal. The mixture was then chilled to 5° C. and a solution of (S)(–)-N-(1,2,3,4-tetrahydro-4-keto-1 -naphthyl)-N-methylformamide (5 g) in dry toluene (100 ml) was added over 10 minutes. After being stirred for 22 hours the resulting mixture was poured into 10% aqueous ammonium chloride solution (200 ml). The phases were separated, the aqueous layer was washed with toluene (25 ml) and the combined organic layers were evaporated under vacuum to give a mixture of cis-(1S,4R)- and trans-(1S,4S)-enantiomers (ratio 87:13 respectively by nmr spectroscopy techniques) as a dark oil (11.7 g), which was chromatographed on silica (500 g). Elution with hexane-ethyl acetate mixtures (1:2 to 1:4) gave the title compound as a foam (3.52 g, 40.8%); Rf 0.37 (silica; ethyl acetate) and 0.50 (silica; chloroform, methanol; 95:5) which was sufficiently pure for use in the next step.

A small reference sample of purified product was obtained by slow crystallisation from a diethyl ether-hexane mixture (6:4). The title compound was obtained as off-white crystals, m.p. 124°–126° C., $[\alpha]_D$+ 21.9° (c=0.5, EtOH). Found: C,61.54; H,4.73; N,3.92. $C_{18}H_{17}Cl_2NO_2$ requires C,61.72; H,4.89; N,4.00%.

EXAMPLE 11

(S)(–)-N-[4-(3,4-Dichlorophenyl)-1,2-dihydro-1-naphthyl]-N-methylformamide

A solution of (1S,4R) (+)-N-[4-(3,4-dichlorophenyl)-1,2, 3,4 -tetrahydro-4-hydroxy-1-naphthyl]-N-methylformamide (2 g) in glacial acetic acid (20 ml) was treated with boron trifluoride etherate (0.8 ml) and stirred for 1 hour at ambient temperature. The solution was poured into water (40 ml), extracted with chloroform (2×20 ml) and the combined chloroform extracts were backwashed with saturated aqueous sodium bicarbonate solution (3×20 ml). The chloroform solution was evaporated under vacuum and the residual glassy solid (2.03 g) was chromatographed on silica (100 g) eluting with hexane-ethyl acetate mixtures (1:1 to 1:4). Evaporation under vacuum of the requisite fractions gave the product as a glass (0.90 g, 47.4%), Rf 0.24 (silica; chloroform); $[\alpha]_D$–50° (c=0.5, EtOH). Found: C, 64.93; H,4.80; N,3.83. $C_{18}H_{15}Cl_2NO$ requires C,65.08; H,4.55; N,4.22%.

$^1$H-nmr (300 MHz, CDCl$_3$)

δ= 2.57–2.84 (m, 2H), 2.89 and 2.94 (2 NMe rotamer singlets, 3H), 4.90–4.99 and 5.82–5.91 (2 rotamer multiplets, 1H), 6.07–6.14 (m, 1H), 7.00–7.55 (m, 7H), 8.19 and 8.30 (2 formyl CH rotamers, 1H) p.p.m.

EXAMPLE 12 cis-(1S,4S)(+)-N-[4-(3,4-Dichlorophenyl)-1,2,3,4 -tetrahydro-1-naphthyl]-N-methylformamide A solution of (S)(–)-N-[4-(3,4-dichlorophenyl)-1,2-dihydro-1-naphthyl] -N-methylformamide (0.64 g) in tetrahydrofuran (10 ml) was hydrogenated over platinum oxide (0.13 g) at room temperature and 50 p.s.i. (3.45 bar) for 1.5 hours. The catalyst was removed by filtration and the filtrate was evaporated under vacuum to give the crude product as a gum (0.62 g, 96.9%). A $^1$H-nmr assay (300 MHz, CDCl$_3$) of this material showed it to be an 88:12 mixture of the required (1S, 4S) cis-isomer (δ=4.19–4.27 ppm, m, for the H$_4$ proton) and the (1S, 4R) trans-isomer (δ=4.05–4.14 ppm, m, for the H$_4$ proton), respectively.

The separation of cis- and trans-isomers is most efficiently effected after removal of the formyl group. However, crystallisation of a sample of the crude product from an ethyl acetate-hexane mixture (1:7) provided a reference sample of the title compound as white microcrystals, m.p. 86°–87° C.; Rf 0.65 (silica; chloroform, methanol; 95:5); $[\alpha]_D$+24.3° (c=0.57, EtOH). Found: C,64.02; H,5.16; N,4.17. $C_{18}H_{17}Cl_2NO$ requires C,64.67; H,5.13; N,4.19%.

$^1$H-nmr (300 MHz, CDCl$_3$)

δ=1.72–1.87 (m, 1H), 1.89–2.15 (m, 2H), 2.26–2.40 (m, 1H), 2.75 and 2.79 (2 NMe rotamer singlets, 3H), 4.19–4.27

(m, 1H), 4.74–4.83 and 5.72–5.80 (2 rotamer multiplets, 1H), 6.79–7.40 (m, 7H), 8.30 and 8.35 (2 formyl CH rotamers, 1H) p.p.m.

EXAMPLE 13 cis-(1S,4S)(+)-N-Methyl-4-(3,4-dichlorophenyl)-1,2,3,4-tetrahydro-1-naphthylamine hydrochloride (sertraline hydrochloride)

A solution of cis-(1S,4S)(+)-N-[4-(3,4-dichlorophenyl)-1,2,3,4-tetrahydro-1-naphthyl]-N-methylformamide (0.35 g of 88:12 cis-trans mixture from Example 12 ) in 2-propanol (3.5 ml) was treated with concentrated aqueous hydrochloric acid (1.05 ml) and heated under reflux for 6 hours. The solution was refrigerated overnight and a first crop of product collected by filtration (0.126 g). The filtrate was concentrated to a third of its volume, diluted with hexane (1 ml), refrigerated overnight and filtered to give a second crop of product (0.134 g). The two crops were combined and slurried in 2-propanol (1 ml) overnight. Filtration gave the product (0.25 g, 69.4%) as white crystals, m.p. 237°–240° C.; $[\alpha]_D$+40.6° (c=1.0, N/20 methanolic HCl).

N.B.

N-Methyl-1,2,3,4-tetrahydro-1-naphthylamine (compound VA) is obtainable according to Coil. Czech. Chem. Commun., 1973, 38, 1159.

I claim:

1. A process for the preparation of the substantially geometrically pure cis-stereoisomeric form of a compound of the formula:

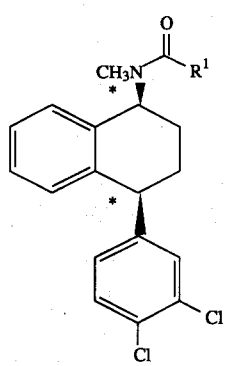

(I)

wherein $R^1$ is H or $C_1$–$C_4$ alkyl and * denotes an unresolved asymmetric centre, which comprises catalytic hydrogenation of a compound of the formula:

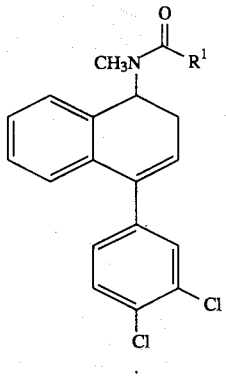

(III)

wherein $R^1$ is as defined for formula (I) .

2. A process for the preparation of the sustantially geometrically and optically pure cis-stereoisomeric form of a compound of the formula:

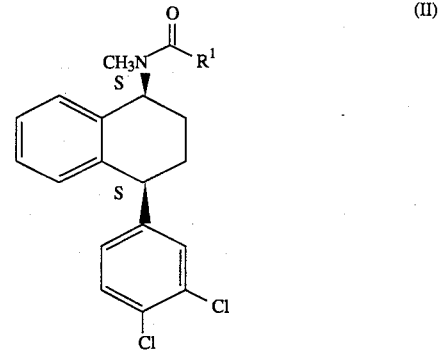

(II)

wherein $R^1$ is H or $C_1$–$C_4$ alkyl and S represents the absolute configuration of a resolved asymmetric centre, which comprises catalytic hydrogenation of a compound of the formula:

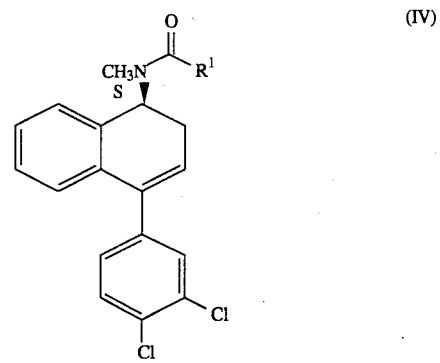

(IV)

wherein $R^1$ and S are as defined for formula (II).

3. A process as claimed in claim 1 wherein the hydrogenation catalyst is platinum or palladium.

4. A process as claimed in claim 3 wherein the hydrogenation catalyst is platinum.

5. A process as claimed in claim 1 wherein $R^1$ is H or methyl.

6. A process as claimed in claim 2 wherein the hydrogenation catalyst is platinum or palladium.

7. A process as claimed in claim 6 wherein the hydrogenation catalyst is platinum.

8. A process as claimed in claim 2 wherein $R^1$ is H or methyl.

9. The substantially geometrically pure cis-stereoisomeric form of a compound of the formula:

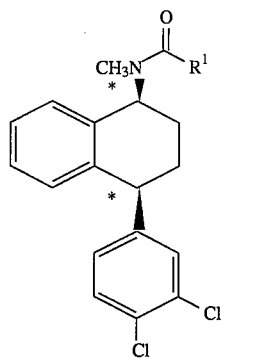

wherein $R^1$ is H or $C_1$–$C_4$ alkyl and * denotes an unresolved asymmetric centre.

10. The substantially geometrically and optically pure cis-stereoisomeric form of a compound of the formula:

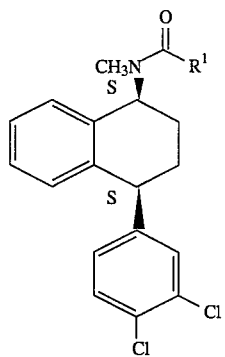

wherein $R^1$ is H or $C_1$–$C_4$ alkyl and S represents the absolute configuration of a resolved asymmetric centre.

11. A compound as claimed in claim 9 wherein $R^1$ is H or methyl.

12. A compound as claimed in claim 10 wherein $R^1$ is H or methyl.

13. A compound of the formula:

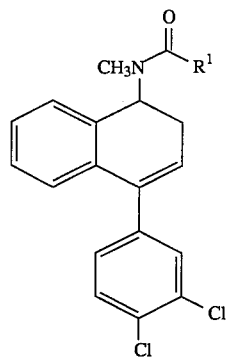

wherein $R^1$ is H or $C_1$–$C_4$ alkyl.

14. A compound as claimed in claim 13 wherein $R^1$ is H or methyl.

15. A compound of the formula:

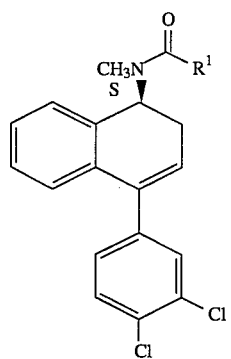

wherein $R^1$ is H or $C_1$–$C_4$ alkyl and S represents the absolute configuration of a resolved asymmetric centre.

16. A compound as claimed in claim 15 wherein $R^1$ is H or methyl.

* * * * *